US012337017B2

United States Patent
Adams et al.

(10) Patent No.: US 12,337,017 B2
(45) Date of Patent: Jun. 24, 2025

(54) MICROBIOTA TRANSFER THERAPY FOR PITT HOPKINS SYNDROME

(71) Applicant: Arizona Board of Regents, Tempe, AZ (US)

(72) Inventors: James Adams, Tempe, AZ (US); Rosa Krajmalnik-Brown, Chandler, AZ (US); Audrey Davidow, Studio City, CA (US)

(73) Assignees: Arizona Board of Regents on Behalf of Arizona State University, Tempe, AZ (US); Pitt Hopkins Research Foundation, Winston-Salem, NC (US)

( * ) Notice: Subject to any disclaimer, the term of this patent is extended or adjusted under 35 U.S.C. 154(b) by 541 days.

(21) Appl. No.: 17/604,972

(22) PCT Filed: Apr. 20, 2020

(86) PCT No.: PCT/US2020/028997
§ 371 (c)(1),
(2) Date: Oct. 19, 2021

(87) PCT Pub. No.: WO2020/215080
PCT Pub. Date: Oct. 22, 2020

(65) Prior Publication Data
US 2022/0211771 A1    Jul. 7, 2022

Related U.S. Application Data

(60) Provisional application No. 62/836,404, filed on Apr. 19, 2019.

(51) Int. Cl.
*A61K 35/74* (2015.01)
*A61P 25/28* (2006.01)

(52) U.S. Cl.
CPC .............. *A61K 35/74* (2013.01); *A61P 25/28* (2018.01)

(58) Field of Classification Search
None
See application file for complete search history.

(56) References Cited

U.S. PATENT DOCUMENTS

| 2010/0210555 A1 | 8/2010 | Bevec |
| 2016/0271189 A1 | 9/2016 | Cutcliffe |
| 2018/0326915 A1 | 11/2018 | Dickinson |
| 2018/0328915 A1 | 11/2018 | Maher |

FOREIGN PATENT DOCUMENTS

| WO | 2015100409 A2 | 7/2015 |
| WO | 2017075098 A1 | 5/2017 |
| WO | 2017218681 A1 | 12/2017 |
| WO | 2020065583 A1 | 4/2020 |

OTHER PUBLICATIONS

Sweatt, "Pitt-Hopkins Syndrome: intellectual disability due to loss of TCF4-regulated gene transcription", Experimental and Molecular Medicine, vol. 45, e21, p. 1-15. (Year: 2013).*
Zollino et al., "Diagnosis and management in Pitt-Hopkins syndrome", Clinical Genetics, vol. 95, 462-478. (Year: 2019).*
Kang D-W, Park JG, Ilhan ZE, Wallstrom G, LaBaer J, Adams JB, Krajmalnik-Brown R, Reduced incidence of Prevotella and other fermenters in intestinal microflora of autistic children, PLoS One, Jul. 3, 2013; 8(7).
Krajmalnik-Brown, R, Lozupone C, Kang DW, Adams J.B., Gut bacteria in children with Autism Spectrum Disorders: Challenges and promis of studying how a complex community influences a complex disease, Microbial Ecology in Health & Disease 2015, 26: 26914.
Kang DW, Adams JB, Gregory AC, Borody T, Chittick L, Fasano A, Khoruts A, Geis E, Maldonado J, McDonough-Means S, Pollard EL, Roux S, Sadowsky MJ, Lipson KS, Sullivan MB, Caporaso JG, Krajmalnik-Brown R, Microbiota Transfer Therapy alters gut ecosystem and improved gastrointestinal and autism symptoms: an open-label study, Microbiome, Jan. 23, 2017; 5(1): 10. Doi: 10.1186/s40168-016-0225-7.
International Search Report and Written Opinion issued in corresponding Application No. PCT/US2020/028997 on Jul. 17, 2020, 9 pages.

* cited by examiner

*Primary Examiner* — Michelle F. Paguio Frising
*Assistant Examiner* — Grant C Currens
(74) *Attorney, Agent, or Firm* — Polsinelli PC

(57) ABSTRACT

Provided herein are compositions and methods for treating Pitt Hopkins Syndrome (PTHS) by restoring PTHS patient's gut microbiota. These methods can be used with PTHS patient with or without ongoing gastrointestinal symptoms. The methods comprise administering a therapeutic composition comprising a fecal microbe or a fecal microbe preparation to the subject.

19 Claims, 2 Drawing Sheets

FIG. 2

| THE BRISTOL STOOL FORM SCALE | | |
|---|---|---|
| Type 1 | | Separate hard lumps, like nuts |
| Type 2 | | Sausage-like but lumpy |
| Type 3 | | Like a sausage but with cracks in the surface |
| Type 4 | | Like a sausage or snake, smooth and soft |
| Type 5 | | Soft blobs with clear-cut edges |
| Type 6 | | Fluffy pieces with ragged edges, a mushy stool |
| Type 7 | | Watery, no solid pieces |

MICROBIOTA TRANSFER THERAPY FOR PITT HOPKINS SYNDROME

CROSS-REFERENCE TO RELATED APPLICATIONS

This application is a U.S. National Stage Application of International Application No. PCT/US2020/028997, filed Apr. 20, 2020, which claims the benefit of U.S. Provisional Patent Application No. 62/836,404 filed Apr. 19, 2019, the entire disclosures of which are herein incorporated by reference.

FIELD OF THE INVENTION

The present disclosure provides compositions and methods for treating a subject diagnosed with Pitt Hopkins Syndrome (PTHS).

BACKGROUND OF THE INVENTION

Pitt Hopkins Syndrome (PTHS) is a rare genetic neurodevelopmental disorder which is caused by a mutation of the TCF4 gene on the 18th chromosome. It is usually a very severe disorder, resulting in major developmental delays, intellectual disability, language impairments, impaired motor function and balance, breathing abnormalities, seizures, and chronic gastrointestinal problems. Most people with PTHS never talk and many never walk. Many people with PTHS are also diagnosed with autism spectrum disorder (ASD), but they are clearly distinct disorders. PTHS affects approximately 1000 people in the US.

Among other symptoms, PTHS patients suffer from chronic and often severe gastrointestinal problems, especially chronic constipation and abdominal pain, which are often lifelong. Many PTHS patients have a frequent need for laxatives, enemas, and sometimes trips to the emergency room or hospital for severe impaction. These GI problems often also result in significant abdominal pain and discomfort, altered gut motility and nutrient absorption with potential for metabolic impact upon the overall functioning of the person. All result in a decreased quality of life.

A need therefore exists for treatments for PTHS, and especially for the debilitating gastrointestinal symptoms of the disease.

SUMMARY OF THE INVENTION

One aspect of the present disclosure encompasses a method for treating Pitt Hopkins syndrome (PTHS) in a subject in need thereof. The method comprises administering to the subject an amount of a pharmaceutical composition effective for treating PTHS. The pharmaceutical composition comprises a fecal microbe preparation.

The subject can range in age from about two years old to adulthood, and can further be diagnosed with autism spectrum disorder (ASD). Alternatively, the subject can range in age from about two years old to adulthood. Further, the subject can exhibit one or more symptoms of GI disorder prior to initiating said treatment. The GI disorder can be diarrhea, abdominal pain, or constipation, and can be chronic.

The fecal microbe preparation can comprise a complete community of microbes obtained from a single healthy donor. For instance, the fecal microbe preparation can be full spectrum microbiota (FSM°). Alternatively, the fecal microbe preparation can comprise a synthetic fecal composition of predetermined microbes. The microbes can be in proportional content that resembles a normal healthy human fecal flora. In some aspects, the fecal microbe preparation is minimally manipulated total fecal microbiota obtained from a subject selected for high diversity of gut bacteria, high amount of *Prevotella*, high amounts of commensal Clostridia species, or a combination thereof. In other aspects, the fecal microbe preparation is a synthetic preparation comprising a high diversity of gut bacteria, high amount of *Prevotella*, high amounts of commensal Clostridia species, or a combination thereof.

The method can further comprise pretreating the subject before administering the fecal microbe preparation. Pretreating the subject can comprise treating the subject with an antibiotic. The antibiotic can be a non-absorbable antibiotic such as vancomycin. The subject can be treated with the antibiotic for 10 days.

Pretreating the subject can further comprise cleansing the bowel of the subject. The bowel can be cleansed by ingestion of magnesium citrate. The bowel can also be cleansed by ingestion of polyethylene glycol, magnesium citrate, or a combination thereof. Pretreating the subject can further comprise fasting for one or more days.

In some aspects, pretreating the subject comprises administering an antibiotic, cleansing the bowel of the subject, fasting, or a combination thereof. In one aspect, pretreating the subject comprises administering to the subject vancomycin for 10 days, fasting for up to one day; cleansing the bowel of the subject by ingestion of magnesium citrate; or a combination thereof.

One or more than one dose of the fecal microbe preparation can be administered to the subject. The one or more doses can be high doses of microbiota. The high dose of the fecal microbe preparation can be about $5 \times 10^{11}$ cells and can be administered daily or b.i.d. The one or more high doses can be administered for 4 days.

The high dose of the fecal microbe preparation can be followed by one or more low doses of the fecal microbe preparation. The one or more low doses can be about $1 \times 10E^{10}$ cells and can be administered every four days. The low doses of the fecal microbe preparation are administered every four days for about 12 weeks. In some aspects, administering the fecal microbe preparation comprises four days of administering a high dose of the fecal microbe preparation, followed by 12 weeks or more of a low dose of the fecal microbe preparation every four days. The fecal microbe preparation can be lyophilized.

The microbe preparation is administered orally such as a solid dosage form selected from the group consisting of capsule, tablet, powder, and granule. In one aspect, the fecal microbe preparation is formulated as an acid resistant capsule. The microbe preparation can also be administered rectally by endoscopy or rectal enema.

The subject can exhibit at least a 10% reduction in PTHS symptom severity after the treatment as compared to the severity of PTHS symptom before initiating the treatment. The subject can also exhibit at least a 20% reduction in PTHS symptom severity at 2 years after treatment as compared to the severity of PTHS symptom before initiating the treatment. The severity of the symptoms can be measured using one of the Parent Global Impressions of PTHS—Revised (PGI-PTHS) the clinical global impression (CGI) tool for PTHS symptoms (CGI-PTHS), the revised Face Legs Activity Crying Consolability Pain Questionnaire for Children with Cognitive Impairment (FLACC), or combinations thereof.

The microbiome diversity in the subject can be reduced by 25% below the microbiome diversity of a neurotypical subject. Using the instant methods, the microbiome diversity can be restored to normal levels after treatment when compared to levels at start of treatment when compared to the microbiome diversity in neurotypical individuals. Further, the diversity is maintained for at least 2 years from start of treatment. The diversity can be assessed using a non-phylogenetic metric, observed OTUs, a phylogenetic distance (PD) index, or combinations thereof.

The subject can exhibit at least a 30% reduction of GI symptoms when a method is used. The reduction of gastrointestinal (GI) symptoms can be maintained for at least 2 years from start of treatment. In one aspect, the subject exhibits at least a 20% reduction in GI symptoms severity at 2 years after treatment as compared to the severity of GI symptoms before initiating the treatment. The severity of the GI disorder can be assessed using the Daily Stool and Symptom Record; the clinical global impression (CGI) tool for GI symptoms (CGI-GI); the Gastrointestinal Symptom Rating Scale (GSRS); or combinations thereof.

Another aspect of the present disclosure encompasses a method of reducing the symptoms of gastrointestinal (GI) problems in subjects having PTHS and GI problems. Yet another aspect of the present disclosure encompasses a method of normalizing phylogenetic diversity of fecal microbiota in subjects having PTHS and GI problems. The method can be as described above.

One aspect of the present disclosure encompasses a kit for performing the method of claim 1, the kit comprising: (a) a fecal microbe preparation effective for treating PTHS; and (b) instructions for (i) preparing the pharmaceutical composition and (ii) administering the composition to a subject in need thereof.

BRIEF DESCRIPTION OF THE FIGURES

FIG. 2. The Bristol Stool Form Scale.

DETAILED DESCRIPTION

Figure 1:
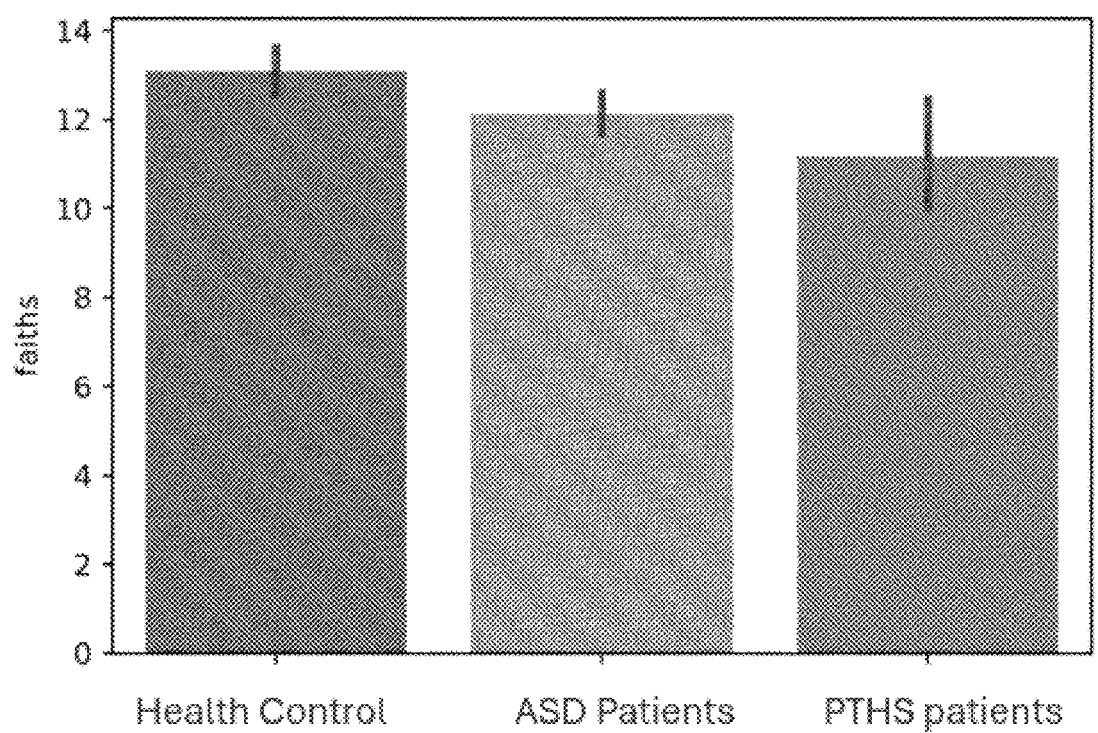
FIG. 1 Faith phylogenetic diversity from swab samples of 171 health controls (Left Panel), 336 ASD patients (Middle Panel) and 32 PTHS patients (Right Panel).

The present disclosure is based in part on the surprising discovery that administration of a fecal microbe preparation to a subject diagnosed or suspected of having or developing PTHS can improve the symptoms of PTHS. The methods can also improve symptoms of gastrointestinal disorders and normalize the diversity of microbiota in the subject.

I. Methods

One aspect of the present disclosure encompasses a method for treating Pitt Hopkins syndrome (PTHS) in a subject in need thereof.

(a) Subject

The subject can be, without limitation, a human, a non-human primate, a mouse, a rat, a guinea pig, or a dog. In some aspects, the subject is a human subject. The subject can be a premature newborn, a term newborn, a neonate, an infant, a toddler, a young child, a child, an adolescent, a pediatric patient, or a geriatric patient. In one aspect, the subject is an adult patient. In another aspect, the subject is an elderly patient. In another aspect, the subject is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In some aspects, the subject is a child patient below about 18, 15, 12, 10, 8, 6, 4, 3, 2, or 1 year old. In one aspect, the subject is a child ranging in age from about birth to about 10 years of age. Alternatively, the subject can range in age from about two years old to adulthood.

A subject is for example one in need of treatment for PTHS. PTHS can be caused by a mutation of the TCF4 gene on the 18th chromosome. However, there are still individuals with a phenotype that cannot be distinguished from PTHS and in whom no mutation can be found. Furthermore, there are individuals with a variant in TCF4, but with a phenotype that differs markedly from the PTHS phenotype. Therefore, a subject can be diagnosed using genetic screening, and in addition to or instead of genetic screening, the subject can be diagnosed using clinical diagnostic criteria for PTHS such as the Clinical Diagnostic Criteria from the International Consensus Report (Zollino et al 2019, "Diagnosis and management in Pitt-Hopkins syndrome: First international consensus statement." Clin Genet. 2019 April; 95(4):462-478).

Many people with PTHS are also diagnosed with autism spectrum disorder (ASD). As such, in some aspects, the subject in need of treatment is also diagnosed with ASD. Several screening instruments are known in the art for evaluating the social and communicative development of a subject with ASD and thus can be used as aids in screening for and detecting changes in the severity of impairment in communication skills, social interactions, and restricted, repetitive, and stereotyped patterns of behavior characteristic of autism spectrum disorder. Evaluation can include neurologic and genetic assessment, along with in-depth cognitive and language testing. Additional measures developed specifically for diagnosing and assessing autism include the Autism Diagnosis Interview-Revised (ADI-R), the Autism Diagnostic Observation Schedule (ADOS-G) and the Childhood Autism Rating Scale (CARS).

Of note are the symptoms of chronic gastrointestinal symptoms similar to Irritable Bowel Syndrome (IBS) in PTHS subjects, especially chronic constipation, diarrhea, or alternation between diarrhea and constipation, which are often lifelong. Many PTHS patients have a frequent need for laxatives, enemas, and sometimes trips to the emergency room or hospital for severe impaction. These GI problems often also result in significant abdominal pain and discomfort, altered gut motility and nutrient absorption with potential for metabolic impact upon the overall functioning of the person. All result in a decreased quality of life. Non-limiting examples of GI problems of the subject include constipation, diarrhea, abdominal pain, irritable bowel syndrome, hemorrhoids, anal fissures, perianal abscesses, anal fistula, diverticular disease, colon polyps and cancer, colitis such as ulcerative colitis, Crohn's disease, ischemic colitis, and radiation colitis. In some aspects, the subject has a GI problem selected from diarrhea, abdominal pain, constipation, or a combination thereof.

Accordingly, a subject in need of treatment can exhibit one or more symptoms of gastrointestinal (GI) disorders. Alternatively, subjects appropriate for treatment according to a method provided herein may not present with or report GI distress symptoms prior to initiating a method as provided herein. In some aspects, a human subject appropriate for treatment according to a method provided herein manifests no gastrointestinal symptoms prior to or at the time at which treatment is begun.

In some aspects, a subject in need of treatment exhibits symptoms of abdominal pain, diarrhea, constipation, or alternating between diarrhea and constipation. In one aspect, the symptoms are chronic. For instance, a subject can suffer from a GI disorder for a period of 1 week, 1 month, 6 months, 1 year, 2 years, or longer. In some aspects, the GI symptoms comprise five or more abnormal days out of 14 days, wherein an abnormal day is a day involving one or more of the type 1-2 (hard) or type 6-7 (soft/liquid) on the Bristol Stool Scale, three or more bowel movements in 1 day, no bowel movement that day, significant abdominal/gastrointestinal pain, required GI medication or treatment such as laxative, or enema.

Regardless of the presence or absence of gastrointestinal distress symptoms, human subjects appropriate for the methods provided herein can have significantly reduced biodiversity of gut microorganisms before the method of treatment as compared to a neurotypical human. The microbial taxonomic and functional diversity present within an individual's fecal microbiota of a fecal microbe preparation is believed to be a factor-influencing outcome following a fecal transplant. As such, a higher diversity of gut microbe in the preparation can be beneficial. The taxonomic diversity can be assessed at the level of kingdom-, phylum-, class-, order-, family-, genus-, and species-levels. By way of example, the approximate composition of major types or kinds of fecal microbes is as follows: Bacteriodetes; *Prevotella; Xylanibacter; Facaelibacterium; Eubacterium; Subdoligramdum; Parabacteriodetes; Clostridium leptum; Clostridium coccoides; Ruminococcus; Collinsella; Roseburia; Akkermansia; Veillonella; Bifidobacterium; Verrucomicrobia; Lactobacillus; Escherichia* (from the Enterobacteriaceae family); *Desulfovibrio; Saccharomyces boulardii; Cladosporium, Pentatrichomona, Chilomastix; Entamoeba dispar* and various gut viruses (e.g., phages).

In some aspects, the subject exhibits at least about 20%, 30%, 40%, 50%, 60%, 70%, 80%, or 90% reduced diversity of gut microorganisms prior to administration of the purified fecal microbiota dosage as compared to a neurotypical human. In some aspects, the microbiome diversity in the subject is reduced by 25% below the microbiome diversity of a neurotypical subject.

The diversity of the microbiome of a subject can be assessed using any one or more methods of assessing microbiome diversity as known in the art. Non-limiting examples of methods of assessing the diversity of a microbiome include a non-phylogenetic metric, observed operational taxonomic units (OTU), Shannon and Simpson diversity indices, and a phylogenetic distance (PD) index. In some aspects, the diversity of a fecal microbe preparation is determined using a non-phylogenetic metric, observed operational taxonomic units (OTU), and a phylogenetic distance (PD) index. The diversity index can be calculated at the phylum level, the family level, the genus level, and/or the species level.

(b) Administration

The method comprises administering to the subject a pharmaceutical composition comprising a fecal microbe preparation. A fecal microbe preparation comprises fecal microorganisms. Fecal microorganisms can be any microorganism or community of microorganisms present in a subject's feces. Fecal microbiota, fecal microorganisms, and fecal microbe preparations can be as described in International Publication No. WO2016191356, the disclosure of which is incorporated herein in its entirety.

A fecal microbe preparation can be a synthetic preparation of predetermined fecal microbes. For instance, a fecal microbe preparation can be a synthetic preparation comprising one or more, two or more, three or more, four or more, or five or more isolated, purified, or cultured fecal microorganisms. A fecal microbe preparation can also be a fecal mixture of microorganisms obtained from a donor. A donor can be a healthy, carefully screened, neurotypical human donor. The fecal microbiota can be prepared from the feces of a single donor or from multiple donors. Further, the fecal microbiota prepared from feces can comprise a complete community of fecal microbes obtained from a donor. Alternatively, the fecal microbiota prepared from feces can lack one or more microorganisms normally present in a complete community of fecal microbes. A microbiota prepared from feces can also be supplemented, spiked, or enhanced with one or more fecal microorganisms, or can be treated to remove one or more of the fecal microorganisms in the mixture. Additionally, microbiota prepared from feces can be obtained from an individual or groups of individuals selected for high diversity of gut microorganisms, high amounts of specific microorganisms, or low amounts of specific microorganisms. By way of non-limiting example, fecal microbe preparations may contain any one or more species of Acidaminococcus, Akkermansia, Alistipes, Anaerotruncus, *Bacteroides, Eggerthella, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum,* and *Veillonella.*

In some aspects, the therapeutic composition comprises a preparation of flora in proportional content that resembles a normal healthy human fecal flora. In some aspects, the fecal microbe preparation is total fecal microbiota derived from the stool of healthy donors matched in age with the subject. In some aspects, the fecal microbe preparation is minimally manipulated, total fecal microbiota derived from the stool of healthy donors. In one aspect, the fecal microbe preparation is minimally manipulated total fecal microbiota obtained from a subject selected for high diversity of gut microorganisms, high amount of *Prevotella*, high amounts of commensal Clostridia species, or a combination thereof. In another aspect, the fecal microbiota is total fecal microbiota derived from the stool of healthy donors spiked with *Prevotella*, high amounts of commensal Clostridia species, or a combination thereof.

The material from the donors can be purified to remove the majority of non-microorganism material, washed, lyophilized, and encapsulated.

A fecal microbe preparation can be formulated as a pharmaceutical composition to be compatible with its intended route of administration. In general, a fecal microbiome preparation is formulated for oral, rectal administration, or other means of delivery into the GI tract, including infused via naso-duodenal infusion. When formulated for rectal administration, the preparation can be formulated as an enema or via rectal suppository.

When formulated for oral administration, the preparation can be formulated as a geltab, pill, microcapsule, capsule, or tablet or formulated as part of or administered together with a food, a food supplement, a food additive, a dairy-based product, a soy-based product or a derivative thereof, a jelly, or a yogurt.

In one aspect, a therapeutic composition comprises a liquid culture. In another aspect, a therapeutic composition is lyophilized, pulverized, and powdered. A powdered fecal preparation may then be infused, dissolved such as in saline, as an enema. Alternatively, the powder may be encapsulated for oral administration. In one aspect, the powdered microbe preparation is encapsulated for oral administration. These capsules may take the form of enteric-coated and/or acid-resistant microcapsules to protect the microbes from stomach acids.

Preparations generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

The method can further comprise pretreating the subject before administering a composition comprising the fecal microbiota. Pretreating the subject optimally prepares the intestines of the subject for microbiota transplant. Pretreating the subject can comprise fasting, treating the subject with antibiotics, undergoing a bowel cleanse, and combinations thereof. In some aspects, the method further comprises fasting, pretreating the subject with an antibiotic, and a bowel cleanse.

The antibiotic, the dose of the antibiotic, and the duration of administration of the antibiotic can and will vary depending on the antibiotic, the GI disorder of the subject, and can be determined experimentally. Non-limiting examples of an appropriate antibiotic can include rifabutin, clarithromycin, clofazimine, vancomycin, rifampicin, nitroimidazole, chloramphenicol, rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In some aspects, the antibiotic is a non-absorbable antibiotic. In one aspect, the antibiotic is vancomycin.

The antibiotic can be administered for a period of time ranging from about 1 day to about 1 month or from about 5 days to about 2 weeks. In one aspect, the antibiotic is vancomycin and is administered for a period of about 8 to about 12 days. In some aspects, administration of the antibiotic is initiated at least seven days (e.g., at least 7, 9, 10, 12, 14, 18, or 21 days) before the bowel cleanse.

Following administration of an antibiotic, the subject can undergo a bowel cleanse. In some aspects, the bowel cleanse comprises administering to the subject magnesium citrate or a product such as MoviPrep®, a commercial bowel prep for colonoscopy. In one aspect, the bowel cleanse comprises administration of sodium citrate. The cleanse can be preceded by a period of fasting lasting from about less than one day to about 2 days. In one aspect, the period of fasting is one day.

In some aspects, pretreating the subject comprises oral Vancomycin for 10 days, fasting for one day, followed by a magnesium citrate cleanse for one day.

A dose of the fecal microbe preparation can be administered daily, every two days, every three days every four days, weekly, or at longer intervals. In some aspects, the preparation is administered daily. In one aspect, the preparation is administered daily for 1, 2, 3, 4, 5, 6, 7, 8, 9, or 10 consecutive days or longer. The preparation can also be administered twice a day (b.i.d.), or three times a day (t.i.d.).

A dose can and will vary provided the dose provides a therapeutically effective amount of the microbe preparation. In one aspect, a dose comprises about $10^5$, $10^6$, $10^7$, $10^8$, $10^9$, $10^{10}$, $10^{11}$, $10^{12}$, or about $10^{13}$ cells. In one aspect, a pharmaceutically active therapeutic effective dose comprises about $10^5$, $10^6$, $10^7$, $10^8$, $10^9$, $10^{10}$, $10^{11}$, $10^{12}$, or about $10^{13}$ cells. In a further aspect, a pharmacologically active therapeutic effective dose can range from about $10^8$ cells to $10^{14}$ cells, from $10^9$ cells to $10^{13}$ cells, from $10^{10}$ cells to $10^{12}$ cells, from $10^9$ cells to $10^{14}$ cells, from $10^9$ cells to $10^{12}$ cells, from $10^9$ cells to $10^{11}$ cells, from $10^9$ cells to $10^{10}$ cells, from $10^{10}$ cells to $10^{14}$ cells, from $10^{10}$ cells to $10^{13}$ cells, from $10^{11}$ cells to $10^{14}$ cells, from $10^{11}$ cells to $10^{13}$ cells, from $10^{12}$ cells to $10^{14}$ cells, and from $10^{13}$ cells to $10^{14}$ cells.

In some aspects, one or more high doses of the fecal microbe preparation are administered to the subject, followed by one or more low doses of the microbe preparation. A high dose can range from about $10^9$ to about $10^{12}$ cells per dose. In some aspects, a high dose ranges from about $1\times10^{11}$ to about $9\times10^{11}$ cells per dose. A low dose can range from about $10^8$ to about $10^{11}$ cells per dose. In some aspects, a low dose ranges from about $5\times10^9$ to about $5\times10^{10}$ cells per dose. In one aspect, administering the fecal microbe preparation comprises 4 days of administering a high dose of the fecal microbe preparation, followed by 12 weeks or more of a low dose of the fecal microbe preparation every four days.

(c) Treatment

The methods provided herein result in, or are aimed at achieving a detectable improvement in one or more indicators or symptoms of PTHS in a subject suspected of having or at risk of having PTHS. The improvement can be measured as soon as at the conclusion of treatment, and can remain or improve after treatment. For instance, the improvement can be maintained or improved for 1 month, 2 months, 3 months, 4 months, 5 months, 6 months, 7 months, 8 months, 9 months, 10 months, 11 months, 1 year, 2 years 3, years, or for the life of the subject. Using a method of the disclosure, a subject can exhibit at least a 1%, 5%, 10%, 15%, 20%, 30%, 40%, 50% or more reduction in PTHS symptom severity at the end of the treatment. Further, the improvements in symptoms can be maintained or improved after treatment. For instance, a subject can exhibit at least a 10%, 15%, 20%, 25%, 30%, 35%, 40%, 45% or more reduction in PTHS symptom severity at 2 years after treatment as compared to the severity of PTHS symptom before initiating the treatment. In one aspect, the subject exhibits at least a 20% reduction in PTHS symptom severity at 2 years after treatment as compared to the severity of PTHS symptom before initiating the treatment.

A detectable improvement can be assessed by measuring the severity of clinical symptoms of PTHS. The clinical symptoms are measured using diagnostic criteria for PTHS such as the Clinical Diagnostic Criteria from the International Consensus Report (Zollino et al 2019, "Diagnosis and management in Pitt-Hopkins syndrome: First international consensus statement." Clin Genet. 2019 April; 95(4):462-478). The symptom severity can be measured using the Parent Global Impressions of PTHS—Revised (PGI-PTHS) in combination with measures of hyperventilation, daytime apnea, gross motor skills, fine motor skills, ataxia, food allergies, environmental allergies, flusing, and rashes, using the clinical global impression (CGI) tool for PTHS symptoms (CGI-PTHS), using the revised Face Legs Activity Crying Consolability Pain Questionnaire for Children with Cognitive Impairment (FLACC), or combinations thereof. In some aspects, the severity of the symptoms is measured using one of the Parent Global Impressions of PTHS—Revised (PGI-PTHS) the clinical global impression (CGI) tool for PTHS symptoms (CGI-PTHS), the revised Face Legs Activity Crying Consolability Pain Questionnaire for Children with Cognitive Impairment (FLACC), or combinations thereof.

The methods also result in improving or restoring the biodiversity of the microbiome in the subject to normal levels after treatment when compared to levels at start of treatment. The biodiversity can be improved or restored as soon as at the conclusion of treatment, and the improvements can remain or are enhanced even after conclusion of treatment. For instance, the improvement or restoration of biodiversity of the microbiota of the subject can be maintained or improved for 1 month, 2 months, 3 months, 4 months, 5 months, 6 months, 7 months, 8 months, 9 months, 10 months, 11 months, 1 year, 2, years 3, years, or for the life of the subject. In some aspects, the biodiversity of the microbiome of the subject is restored to normal levels after treatment when compared to levels at start of treatment when compared to the microbiome diversity in neurotypical individuals. Yet another aspect of the disclosure encompasses a method of normalizing phylogenetic diversity of fecal microbiota in subjects having PTHS and GI problems. The diversity of the microbiome can be assessed as described above in Section I(a).

The methods can also result in reduction in the severity of GI symptoms in the subject when compared to the severity of GI symptoms in the subject at start of treatment. The severity of symptoms can be reduced by about 5%, 10%, 15%, 20%, 25%, 30%, 35%, 40%, 45%, 50%, 55%, 60%, 65%, 70%, 75%, 80%, 85%, 90%, 95%, or complete recovery from GI symptoms. In some aspects, severity of symptoms are reduced by about 5% to about 50%, about 45% to about 75%, from about 75% to about 90%, or complete recovery from GI symptoms. The severity of GI symptoms can be reduced or GI symptoms can be eliminated as soon as at the conclusion of treatment, and the reductions can remain or are enhanced even after conclusion of treatment. For instance, the reductions in GI symptoms in the subject can be maintained or improved for 1 month, 2 months, 3 months, 4 months, 5 months, 6 months, 7 months, 8 months, 9 months, 10 months, 11 months, 1 year, 2, years 3, years, or for the life of the subject. In one aspect, the subject exhibits at least a 20% reduction in GI symptom severity at 2 years after treatment as compared to the severity of GI symptoms before initiating the treatment.

The GI symptoms can include five or more abnormal days out of 14 days, wherein an abnormal day is a day involving one or more of the type 1-2 (hard) or type 6-7 (soft/liquid) on the Bristol Stool Scale, three or more bowel movements in 1 day, no bowel movement that day, significant abdominal/gastrointestinal pain, GI medication or treatment is required (such as laxative, enema, etc.). The clinical global impression (CGI) tool for GI symptoms (CGI-GI); the Gastrointestinal Symptom Rating Scale (GSRS) the severity of the GI disorder is assessed by the Daily Stool and Symptom Record; the clinical global impression (CGI) tool for GI symptoms (CGI-GI); the Gastrointestinal Symptom Rating Scale (GSRS); or combinations thereof.

As such, another aspect of the disclosure encompasses a method of reducing the symptoms of gastrointestinal (GI) problems in subjects having PTHS and GI problems.

II. Kits

One aspect of the present disclosure encompasses a kit for performing the method of claim 1, the kit comprising: (a) a fecal microbe preparation effective for treating PTHS; and (b) instructions for (i) preparing the pharmaceutical composition and (ii) administering the composition to a subject in need thereof.

As used herein, "kits" refer to a collection of elements including at least one non-standard laboratory reagent for use in the disclosed methods, in appropriate packaging, optionally containing instructions for use. A kit may further include any other components required to practice the methods, such as dry powders, concentrated solutions, or ready-to-use solutions. In some aspects, a kit comprises one or more containers that contain reagents for use in the methods. Containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

A kit may include instructions for using the compositions and preparations for treating PTHS in a subject in need thereof. The instructions will generally include information about the use of the kit in the disclosed methods. In other aspects, the instructions may include at least one of the following: description of possible therapies including therapeutic agents; clinical studies; and/or references. The instructions may be printed directly on the container (when present), or as a label applied to the container, or as a separate sheet, pamphlet, card, or folder supplied in or with the container.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures. In the context of autism spectrum disorder, "treat" and "treating" encompass alleviating, ameliorating, delaying the onset of, inhibiting the progression of, or reducing the severity of one or more symptoms associated with an autism spectrum disorder.

As used herein, a "subject" can be a human or animal including, but not limited to, a dog, cat, horse, cow, pig, sheep, goat, chicken, rodent, e.g., rats and mice, and primate, e.g., monkey. In some aspects subjects are human subjects. The human subject may be a pediatric, adult, or a geriatric subject.

As used herein, a "microbiota" and "flora" refer to a community of microbes that live in or on a subject's body, both sustainably and transiently, including eukaryotes, archaea, bacteria, and viruses (including bacterial viruses (i.e., phage)).

A "fecal microbiota" refers to a community of microbes present in a subject's feces.

As used herein, the terms "fecal microbe preparation" or a "fecal microbiota preparation" refers to a preparation comprising fecal microorganisms. Fecal microorganisms can be any microorganism or community of microorganisms present in a subject's feces.

As used herein, "therapeutically effective amount" or "pharmaceutically active dose" refers to an amount of a composition which is effective in treating the named disease, disorder or condition.

As used herein, "isolated" or "purified" refers to a microorganism or other entity or substance that has been (1) separated from at least some of the components with which it was associated when initially produced (whether in nature or in an experimental setting), and/or (2) produced, prepared, purified, and/or manufactured by the hand of man. Isolated or purified microorganisms can be separated from at least about 10%, about 20%, about 30%, about 40%, about 50%, about 60%, about 70%, about 80%, about 90%, or more of the other components with which they were initially associated.

As used herein, the terms "non-pathogenic" in reference to a bacterium or any other organism or entity includes any such organism or entity that is not capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, "colony forming units" (cfu) refers to an estimate of the number of viable microorganism cells in a given sample. The number of cfu can be assessed by counting the number of colonies on an agar plate as in standard methods for determining the number of viable microorganisms in a sample.

As used herein, "viable" means possessing the ability to multiply. The viability of a population of microorganisms can be monitored as a function of the membrane integrity of the cell. Cells with a compromised membrane are considered to be dead or dying, whereas cells with an intact membrane are considered live. For example, SYTO 9 and propidium iodide are used to stain and differentiate live and dead bacteria. See Stocks, Cytometry A. 2004 October; 61(2): 189-95. Cell viability can also be evaluated via molecular viability analyses, e.g., a PCR-based approach, which can differentiate nucleic acids associated with viable cells from those associated with inactivated cells. See Cangelosi and Mescheke, Appl Environ Microbiol. 2014 October; 80(19): 5884-5891.

As used herein, "Shannon Diversity Index" refers to a diversity index that accounts for abundance and evenness of species present in a given community using the formula $H = -\Sigma_{=1} P_i \ln p_i$, where H is Shannon Diversity Index, R is the total number of species in the community, and $p_i$ is the proportion of R made up of the z'th species. Higher values indicate diverse and equally distributed communities, and a value of 0 indicates only one species is present in a given community. For further reference, see Shannon and Weaver, (1949) The mathematical theory of communication. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As various changes could be made in the above-described cells and methods without departing from the scope of the invention, it is intended that all matter contained in the above description and in the examples given below, shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Treating Children Diagnosed with PTHS Using Microbiota Transfer Therapy (MTT)

Pitt Hopkins Syndrome (PTHS) is a rare genetic neurodevelopmental disorder which is caused by a mutation of the TCF4 gene on the 18th chromosome. It is usually a very severe disorder, resulting in major developmental delays, intellectual disability, language impairments, impaired motor function and balance, breathing abnormalities, seizures, and chronic gastrointestinal problems. Most people with PTHS never talk and many never walk. Many people with PTHS are also diagnosed with autism spectrum disorder (ASD). PTHS affects approximately 1000 people in the US.

Relevant to this study are the symptoms of chronic gastrointestinal symptoms, especially chronic constipation and/or diarrhea, which are often lifelong. Many PTHS patients have a frequent need for laxatives, enemas, and sometimes trips to the emergency room or hospital for severe impaction. These GI problems often also result in significant abdominal pain and discomfort, altered gut motility and nutrient absorption with potential for metabolic impact upon the overall functioning of the person. All result in a decreased quality of life.

The Pitt Hopkins Foundation (a small non-profit formed by parents of children with PTHS in 2012) commissioned the American Gut team to conduct a study of the microbiome in stool samples from 32 people with PTHS. Those samples were compared against 171 controls from the American Gut study, matched by age, country, gender and antibiotic history. The samples were also compared against 336 ASD samples from the American Gut study. The fecal microbiota of subjects in the PTHS group was found to have a significantly lower microbial phylogenetic diversity than the healthy controls, (p=p=0.00054), and lower than the ASD group (p=0.0028); FIG. 1. Also, for the PTHS group, fecal microbiota of those with chronic GI symptoms (constipation or diarrhea) had significantly lower microbial diversity than those without GI symptoms, p=0.04. Lower phylogenetic diversity is generally associated with worse GI health, presumably due to the lack of beneficial bacteria.

In this study, Microbiota Transfer Therapy (MTT) is used for treating patients with Pitt Hopkins Syndrome (PTHS) and gastrointestinal problems similar to Irritable Bowel Syndrome (IBS). MTT involves a combination of 10 days of oral vancomycin (an antibiotic to kill pathogenic bacteria), followed by a bowel cleanse, followed by 12 weeks of Fecal Microbiota (FM) transfer (administration of a fecal microbe preparation).

The mechanisms by which the microbiota affect GI symptoms is an active area of research. Little is known about the gut bacteria of PTHS patients, and how it may relate to GI symptoms. In conditions such as *Clostridium difficile* infections, it appears that an overgrowth of a single bacteria and the toxin they produce is the mechanism of action. For PTHS, there may be a similar type of bacterial infection, and/or a lack of beneficial bacteria. Beneficial bacteria are important for many functions, including digesting food, producing certain vitamins, maintaining water balance, producing short-chain fatty acids such as butyrate (which is a primary food for colonic cells), and competing against pathogenic bacteria. So, MTT could result in a healthier microbiome, which will reduce GI symptoms that include chronic constipation and/or diarrhea, and the pain and discomfort associated with those symptoms. If the microbiome is improved, it is also possible that there may be some effect on some PTHS-related symptoms.

GI pain and discomfort are often a major factor in the quality of life for children with PTHS. Here is a direct quote from Audrey Davidow, a parent of a child with PTHS and director of the Pitt Hopkins Foundation: "Children with PTHS are often in a great deal of abdominal pain. We theorize that the pain receptors in their gut may be overactive. For example, my son has daily pain. I can tell because he's agitated, and sometimes cries because of it. Some children with PTHS wind up in the hospital because they are in so much pain. When my son has a bowel movement the pain decreases, but it can return within a couple of hours depending on how severe it is. Most of our parents would say whenever their child seems uncomfortable or upset—the gut is the first thing to look at."

Eighteen children with PTHS who also have chronic gastrointestinal disorders are treated with microbiota transfer therapy (MTT). The trial includes a 10-day treatment with oral vancomycin (or placebo), then 1 day of magnesium citrate to cleanse the bowel of vancomycin and bacteria/feces (all participants, since its bowel-emptying effect cannot be blinded), followed by oral administration of FM (or placebo). An initial high dose of FM (or placebo) for two days is followed by a lower maintenance dose of FM (or placebo) for 12 weeks.

The combination of oral vancomycin (to reduce pathogenic bacteria), and fasting/magnesium citrate (to further cleanse the bowel) are intended to optimally prepare the intestines for microbiota transplant with fecal microbiota from healthy donors.

Magnesium citrate is used for the bowel cleanse because it is commonly used by patients with PTHS as a laxative, and is well-tolerated by them.

Inclusion Criteria:
1) Children ages 5-17 years with Pitt Hopkins Syndrome (verified by genetic testing).
2) GI disorder as defined below that has lasted for at least 2 years.
3) No changes in medications, supplements, diet, or therapies in last 2 months, and no intention to change them during the Parts 1 and 2 of the clinical trial.
4) Ability to swallow pills (without chewing).
5) Review of last two years of medical records by the study physician.

Exclusion Criteria
1) Antibiotics in last 3 months.
2) Probiotics in last 2 months, or fecal transplant in last 12 months.
3) Tube feeding.
4) Severe gastrointestinal problems that require immediate treatment (life-threatening).
5) Ulcerative Colitis, Crohn's Disease, diagnosed Celiac Disease, Eosinophilic Gastroenteritis, or similar conditions.
6) Unstable, poor health (based on study physician's opinion).
7) Recent or scheduled surgeries.
8) Current participation in other clinical trials.
9) Females who are pregnant or who are at risk of pregnancy and sexually active without effective birth control. A pregnancy test is conducted on all female participants as part of the screening and at each clinical visit.

10) Allergy or intolerance to vancomycin or magnesium citrate.
11) Clinically significant abnormalities at baseline on two blood safety tests: Comprehensive Metabolic Panel, and Complete Blood Count with Differential. Note that some abnormalities may occur due to PTHS, so only those likely to significantly increase risk in this study would be grounds for exclusion, at the discretion of the study physician.

The rational for exclusions 1-2 is that they interfere with gut flora.

The rationale for exclusion 3 is that those individuals are probably less likely to respond to the proposed treatment.

The rationale for exclusions 4-7 is that those individuals are at higher risk of safety problems with MTT.

The rational for exclusion 8 is that participation in other trials would interfere with the results of this one.

The rationale for exclusion 9 is to avoid risk to fetuses.

The rationale for exclusion 10 is to avoid known allergic reactions to study medications.

The rationale for exclusions 11 is to ensure that participants are in adequate health (aside from chronic GI and PTHS-related problems) at the start of the study.

Definition of a GI Disorder (for this Study):

On the Daily Stool and Symptom Record, five or more abnormal days out of 14 days, where an abnormal day is defined as a day which involves one or more of the following symptoms:

Abnormal stool: type 1-2 (hard) or type 6-7 (soft/liquid) on the Bristol Stool Scale.

Three or more bowel movements in 1 day.

No bowel movement that day.

Significant abdominal/gastrointestinal pain.

GI medication or treatment is required (such as laxative, enema, etc.)

Study Design

Table 1: Summary of Study Design

TABLE 1

Summary of Study Design

| | Part 1 | Part 2 | Part 3 |
|---|---|---|---|
| Group A | Treatment | Observation | Observation |
| Group B | Placebo | Treatment | Observation |

Part 1: Treatment

The three treatments (oral vancomycin, magnesium citrate, and Fecal Microbiota) will be given sequentially.

Oral Vancomycin (an oral antibiotic) for 10 days to reduce the amount of pathogenic bacteria, followed by Magnesium citrate (a laxative/bowel cleanse) for one day to remove the vancomycin and further reduce intestinal bacteria, followed by Fecal Microbiota (purified intestinal bacteria from healthy, carefully-screened donors) for 2 weeks. The dosage for the first four days will be approximately $5 \times 10^{11}$ cells/day. It can be administered as a single dose or b.i.d. The maintenance dose for the next 12 weeks will be approximately $1 \times 10^{11}$ cells every four days.

Group A: vancomycin, magnesium citrate, FM

Group B: placebo vancomycin, magnesium citrate, placebo FM (note that this group receives the real magnesium citrate because the bowel-emptying effects are obvious)

Part 2: Open-Label Observation and Cross-Over

Group A: observation only (no treatment) for 14 weeks

Group B: real treatment given in Part 1 to Group A; i.e, vancomycin, magnesium citrate, FM Part 3: Observation: Follow-Up at 14 Weeks after the End of Part 2

Participant duration is 28 weeks for treatment/observation (part 1 and 2), and 14 weeks for follow-up after treatment ends (Part 3).

Study duration is likely 2-3 years, depending on the enrollment rate of participants.

Tables 2-5 describe schedule for Parts 1 and 2 (note that dates might vary by a few days due to patient scheduling issues, but treatment duration is fixed).

Table 2: Part 1: Treatment for Groups A and B

TABLE 2

Part 1: Treatment for Groups A and B

| | | Part 1 | | | |
|---|---|---|---|---|---|
| | Baseline | Days 1-10 | Day 11 | Days 12-14 | Days 15-98 |
| Group A | | Vancomycin | Magnesium Citrate | High-dose FM | Maintenance FM |
| Group B | | Placebo vancomycin | Magnesium Citrate (not placebo) | Placebo FM | Placebo FM |
| Physical Exam, and CGI | Day 0 | | | | Day 98 |
| DSR | Daily for 14 days prior to Day 0 | Daily | | Daily | Daily |
| Vancomycin adverse effect | | Days 1-10 | | | |
| GSRS and PGI-PTHS and FLACC | Day 0 | Day 10 | | | Days 24, 38, 52, 66, 80, 94 |
| Diet Evaluation | Day 0 | | | | |
| Blood, buccal swab | Day 0 | | | | Day 98 |
| Urine, Stool | Day 0 | Day 8 | | | Day 24, 94 |

Table 3: Part 2: Group A: Observation

TABLE 3

Part 2: Group A: Observation

| | Days 99-198 |
|---|---|
| Treatments | none |
| Physical Exam, and CGI | Day 198 |
| DSR | Days 134-148, 180-194 |
| GSRS and PGI-PTHS and FLACC | Days 148, 194 |
| Blood, buccal swab | Day 198 |
| Urine, Stool | Day 198 |
| Days | 99-198 |
| Treatments | none |
| Physical Exam, and CGI | Day 198 |
| DSR | Days 134-148, 180-194 |

Days 99-198
Treatments none
Physical Exam, and CGI Day 198
DSR Days 134-148, 180-194
Table 4: Part 2: Group B: Open-Label Cross-Over

TABLE 4

Part 2: Group B: Open-label cross-over

| | Part 2 | | | |
|---|---|---|---|---|
| | Days 101-110 | Day 111 | Days 112-114 | Days 115-198 |
| Treatments | Vancomycin | Magnesium Citrate | High-dose FM | Maintenance FM |
| Physical Exam, and CGI | | | | Day 198 |
| DSR | Daily | | Daily | Daily |
| Vancomycin adverse effect | Daily Days 101-110 | | | |
| GSRS and PGI-PTHS and FLACC | | Day 110 | | Days 124, 138, 152, 166, 180, 194 |
| Blood, buccal swab | | | | Day 198 |
| Urine, Stool | Day 108 | | | Day 124, 194 |

Table 5: Part 3: Follow-Up at 14 Weeks after End of Part 2 for Groups A and B

TABLE 5

Part 3: Follow-up at 14 weeks after end of Part 2 for Groups A and B

| | Day 296 |
|---|---|
| Phone call with study physician | Day 296 |
| DSR | Daily days 280-294 |
| GSRS and PGI-PTHS; Diet form | Day 296 |
| Urine, Stool | Day 296 |
| Diet Evaluation | Day 296 |

A study coordinator contacts patients on approximately the following dates to check on compliance with the study protocol and to screen for possible adverse events.

Part 1: Both Groups Days 10, 12, 15, 45
Part 2, Group A: Day 150
Part 2, Group B: Day 110, 112, 115, 145
Part 3: Both Groups Day 245

Participants are required to complete a medication checklist to determine their compliance with the study medication. Also, they are required to return medication containers with any unused medication at their clinic appointments.

Dosage for this Study, and Justification:
Vancomycin (oral): 40 mg/kg P.O. per day, maximum of 2 gram P.O. (oral) per day, divided into three doses for 10 days.
Magnesium Citrate (oral): The standard concentration is 1.75 g/30 mL solution. The standard dose is:
5-8 yr: 4 ml/kg-bodyweight
8-12 yr: 150 ml
12-15 yr: 200 ml
15-18 yr: 300 ml Half the standard dose (above) is given in the early afternoon, and followed by another ½ dose within 12 hours if sufficient clean out does not occur after 3-4 hours.

The dosage is modified based on the clinician's assessment of the child's history of GI problems and response to initial mag citrate dose. Evening meal to be clear liquids.

Initial FM Oral Dose: The dosage for the first four days will be approximately $5 \times 10^{11}$ cells/day. It can be administered as a single dose or b.i.d.

Maintenance FM Oral Dose: The maintenance dose for the next 12 weeks will be approximately $1 \times 10^{11}$ cells every four days. All FM doses will be given 2 hours away from meals.

Outcome Measures

Below Table 6 is a chart of the outcome measures, followed by a more detailed description of them. The CGI is conducted by the study physician. All other forms are completed by the participant's parent/guardian, after receiving instructions from the study coordinator.

Table 6: Outcome Measures

TABLE 6

| Outcome Measures | |
|---|---|
| Primary Outcome Measure | Daily Stool Record A 14-day evaluation with the Bristol Stool Form Scale. |
| Secondary Outcome Measures | CGI for GI Disorder CGI for PTHS Symptoms PGI-PTHS GSRS FLACC pain |
| Tertiary/Exploratory Outcome Measures | Microbiome Composition of Stool |
| Possible Future Exploratory Outcome Measures | Metabolomics of Blood, Urine, and Stool Measurements of 200+ metabolites in blood, urine, and stool (samples may be collected for future testing). |

Daily Stool Record (DSR)

For the Daily Stool Record, participants record the type of stool(s) each day using the Bristol Stool Form Scale (FIG. 2). It is scored as the percentage of days (over 14 days) with a normal stool (defined as a stool with a score of 3-5 on the Bristol Stool Form Scale; abnormal scores are 1-2 for very hard stools, and 6-7 for soft/liquid stools). Days without a bowel movement, or with 3 or more bowel movements, are counted as an abnormal day. Days requiring a GI medication/treatment, such as a laxative or enema, are also counted as an abnormal day. Days with significant abdominal pain are also counted as an abnormal day.

The reason for this scale is that most PTHS patients have constipation, but some have diarrhea, and some alternate between the two. This simple form allows us to describe either type of problem as an "abnormal" day, and hence use a single number to describe constipation and/or diarrhea symptoms.

Subscales includes the percentage of days of types 1-2 (constipation), types 6-7 (diarrhea), days with no stool, days with 3 or more stools, days requiring GI medication/treatment, and days with significant abdominal pain.

Clinical Global Impression (CGI)

The CGI is a widely used tool for assessing severity of symptoms, and changes after treatment. The CGI-Severity Scale (CGI-S) is used at baseline, and after treatment the CGI-S, CGI-Improvement (CGI-I) is used, and CGI-Efficacy. The study physician conducts all the CGI evaluations.

Two types of CGI evaluations are conducted. One evaluation focuses on GI symptoms (CGI-GI), and one focuses on PTHS-related symptoms (CGI-PH) not including GI symptoms. Since GI symptoms are distinct from PTHS symptoms, the two are separated by using two different assessments by the study physician.

Parent Global Impressions—Pitt Hopkins (PGI-PTHS)

There is no validated or unvalidated instrument for assessing symptoms in PTHS patients, as this is the first treatment study for PTHS. Therefore, the Parent Global Impressions of PTHS—Revised (PGI-PTHS) is adapted for patients with PTHS. The PGI-PTHS includes 18 different symptoms, and changes in symptoms are rated on a 7-point scale from much worse (−3) to zero (no change) to much better (+3). All of the original 18 items on the PGI-PTHS have also been observed in patients with PTHS. Therefore, the PGI-PTHS is used as an initial basis for the PGI-PTHS. The following 9 items are common in PTHS patients are next added that, based on a discussion with the Pitt Hopkins Foundation:
1. Hyperventilation
2. Daytime Apnea
3. Gross Motor Skills
4. Fine Motor Skills
5. Ataxia (lack of communication between brain and body)
6. Food allergies
7. Environmental allergies
8. Flushing
9. Rashes An advantage of this scale is that it is quick to assess (10 minutes), so parents/guardians use it frequently during the study to gather a quick assessment on possible changes in any PTHS-related symptoms.

Gastrointestinal Symptom Rating Scale (GSRS)

The GSRS is an assessment of GI symptoms based on 15 questions, which are then scored in five domains: abdominal pain, reflux, indigestion, diarrhea, and constipation. GSRS-Likert is used, which rates each symptom on a 7-point scale. The GSRS is somewhat limited in that the scale is qualitative, but it provides good coverage of GI symptoms common in PTHS patients. Since it is not validated for PTHS patients, the scale is used as a secondary outcome.

Revised Face Legs Activity Crying Consolability Pain Questionnaire for Children with Cognitive Impairment (FLACC)

The original FLACC was slightly revised for children with cognitive impairment by modifying the descriptions of some items. It assesses pain in five areas (Face Legs Activity Crying Consolability) using a three-point scale for each area, resulting in total FLACC pain scale ranging from zero to 10. The Interrater reliability has high intraclass correlation coefficients (ICC, ranging from 0.76 to 0.90) and adequate kappa statistics (0.44-0.57). The criterion validity is supported by good correlations between FLACC, parent, and child scores (rho=0.65-0.87; $P<0.001$). The construct validity was demonstrated by a significant decrease in FLACC scores following analgesic administration (6.1+/−2.6 vs 1.9+/−2.7; $P<0.001$) in a small study. So, this scale is useful for assessing pain in children with PTHS.

Diet

The diet evaluation involves an estimate of the frequency of foods consumed during the last week, using the Block Brief 2000 Food Frequency Questionnaire from Nutrition Quest (child). Analysis of the form provides an estimate of both macro and micro nutrient intake. This information is helpful in interpreting results of microbiome measurements. The diet form is repeated at the end of the study, to determine if the treatment also results in changes in diet.

PTHS Registry

The Pitt Hopkins Research Foundation established a registry which collects a detailed 14-page medical history on people with PTHS. Participants fill out that form prior to starting the study to provide the study physician with a detailed understanding of their medical history.

Medical History

This form supplements the PTHS Registry form. It includes medical history focused on onset and history of PTHS and GI symptoms, other medical conditions, recent treatments, current medications/supplements, special diets, and level of exercise.

Clinical Diagnostic Criteria for PTHS

The clinical diagnostic criteria for PTHS are evaluated for each participant using Table 2 of the Clinical Diagnostic Criteria from the International Consensus Report. This is only used for informational purposes, as the verification of PTHS diagnosis is done by review of previous genetic testing of the study participants.

Microbiome Assessments

Microbiome assessments are conducted by assessing the overall diversity of gut bacteria at baseline (before MTT treatment) and how it changes after the treatment is investigated using a non-phylogenetic metric, observed OTUs and a phylogenetic distance (PD) index. Next, individual bacterial profiles are collected at baseline to identify specific bacteria significantly different between PTHS and controls (previously collected). Significant changes in levels of either beneficial or harmful bacteria after MTT treatment are assessed. Similarity of the gut microbiome of the recipients to that of their donor is then assessed to determine the successful of engraftment.

What is claimed is:

1. A method for treating Pitt Hopkins syndrome (PTHS) in a subject in need thereof, comprising
administering to the subject a fecal microbe preparation comprising at least $1\times10^9$ cells for at least 12 weeks, thereby reducing severity of PTHS symptoms in the subject by at least 10% as determined by a clinical global impression scale applied to the subject before and after the treatment.

2. The method of claim 1,
wherein the clinical global impression scale is selected from Parent Global Impressions of PTHS—Revised (PGI-PTHS), Clinical Global Impression (CGI) tool for PTHS symptoms (CGI-PTHS), revised Face Legs Activity Crying Consolability Pain Questionnaire for Children with Cognitive Impairment (FLACC), and any combination thereof.

3. The method of claim 1, wherein the subject suffers from gastrointestinal (GI) symptoms selected from abdominal pain, diarrhea, constipation, and any combination thereof.

4. The method of claim 1, wherein the fecal microbe preparation comprises:
(i) a complete community of microbes obtained from a healthy donor;
(ii) a full spectrum microbiome from a healthy donor; and/or
(iii) a manipulated total fecal microbiome obtained from a healthy donor.

5. The method of claim 1, wherein the fecal microbe preparation comprises:
   (i) a synthetic preparation of predetermined fecal microbes;
   (ii) a synthetic fecal composition of predetermined microbes in proportional content that resembles a normal healthy human fecal flora; and/or
   (iii) a synthetic preparation comprising a diversity of gut bacteria comprising at least *Prevotella*, or commensal Clostridia species.

6. The method of claim 1, further comprising pretreating the subject before administering the fecal microbe preparation.

7. The method of claim 6, wherein the pretreating the subject comprises one or more of: (a) treating the subject with an antibiotic; (b) cleansing the bowel of the subject; and (c) fasting the subject for one or more days.

8. The method of claim 7, wherein (a) the antibiotic is a non-absorbable antibiotic; and/or (b) cleansing the bowel of the subject comprises ingestion of magnesium citrate, polyethylene glycol or a combination thereof.

9. The method of claim 6, wherein the pretreating the subject comprises:
   (a) administering to the subject vancomycin for 10 days;
   (b) fasting the subject for up to one day;
   (c) cleansing the bowel of the subject by ingestion of magnesium citrate; or
   (d) a combination thereof.

10. The method of claim 1, wherein the fecal microbe preparation is administered to the subject in one or more high doses; and/or in one or more low doses;
    wherein the one or more high doses each comprises more than $10^{11}$ cells but fewer than $10^{12}$ cells in the fecal microbe preparation; and
    wherein the one or more low doses each comprises more than $10^9$ cells but fewer than $10^{11}$ cells in the fecal microbe preparation.

11. The method of claim 10, wherein
    (a) the one or more high doses of the fecal microbe preparation each comprises more than $10^{11}$ cells but fewer than $9 \times 10^{11}$ cells and is administered daily or two times a day; and/or
    (b) the one or more high doses are administered for 4 days.

12. The method of claim 10, wherein administering the one or more high doses of the fecal microbe preparation is followed by administering the one or more low doses of the fecal microbe preparation.

13. The method of claim 12, wherein
    (a) the one or more low doses of the fecal microbe preparation each comprises more than $5 \times 10^9$ cells but fewer than $10^{11}$ cells; and/or
    (b) the one or more low doses of the fecal microbe preparation are administered every four days for at least 12 weeks.

14. The method of claim 1, wherein the fecal microbe preparation is lyophilized.

15. The method of claim 1, wherein the fecal microbe preparation is administered orally, optionally as a solid dosage form selected from the group consisting of capsule, tablet, powder, and granule, or is administered rectally by endoscopy or rectal enema.

16. The method of claim 15, wherein the fecal microbe preparation is formulated as an acid-resistant capsule.

17. The method of claim 1, wherein:
    (a) the subject exhibits at least a 20% reduction in severity of PTHS symptoms at 2 years after the treatment as compared to the severity of PTHS symptoms before initiating the treatment;
    (b) the microbiome diversity in the subject is restored to the microbiome diversity level of a neurotypical individual; or
    (c) the subject exhibits at least a 30% reduction in severity of GI symptoms, optionally, maintained for at least 2 years from the start of the treatment.

18. The method of claim 17, wherein
    (a) the severity of the PTHS symptoms is measured using one or more scales selected from Parent Global Impressions of PTHS—Revised (PGI-PTHS), clinical global impression (CGI) tool for PTHS symptoms (CGI-PTHS), and revised Face Legs Activity Crying Consolability Pain Questionnaire for Children with Cognitive Impairment (FLACC);
    (b) the microbiome diversity is assessed using a non-phylogenetic metric, observed operational taxonomic units (OTUs), a phylogenetic distance (PD) index, or any combination thereof; and/or
    (c) the severity of the GI symptoms is assessed using Daily Stool and Symptom Record, clinical global impression (CGI) tool for GI symptoms (CGI-GI), Gastrointestinal Symptom Rating Scale (GSRS), or any combination thereof.

19. A method of normalizing phylogenetic diversity of fecal microbiota in a subject having PTHS and experiencing gastrointestinal (GI) symptoms, comprising
    administering to the subject a fecal microbe preparation comprising at least $1 \times 10^9$ cells for at least 12 weeks, thereby reducing severity of the subject's GI symptoms by at least 20% as assessed by Daily Stool and Symptom Record, clinical global impression (CGI) tool for GI symptoms (CGI-GI), Gastrointestinal Symptom Rating Scale (GSRS), or any combination thereof.

* * * * *